| United States Patent [19] | [11] Patent Number: 5,061,555 |
| Edenbaum et al. | [45] Date of Patent: Oct. 29, 1991 |

[54] WATER-ACTIVATED ORTHOPEDIC CAST COMPOSITION HAVING COLORANT

[75] Inventors: Martin Edenbaum, Princeton Junction, N.J.; Kurt C. Frisch, Grosse Ile, Mich.; Aisa Sendijarevic, Troy, Mich.; Shaio-wen Wong, Claire Shores, Mich.

[73] Assignee: Carapace, Inc., Tulsa, Okla.

[21] Appl. No.: 540,531

[22] Filed: Jun. 19, 1990

Related U.S. Application Data

[63] Continuation-in-part of Ser. No. 452,217, Dec. 18, 1989.

[51] Int. Cl.$^5$ .................. A61L 15/14; A61F 5/04; A61F 13/04; B32B 17/04

[52] U.S. Cl. .................. 428/253; 128/90; 428/254; 428/255; 428/273; 428/542.8; 428/913; 523/105

[58] Field of Search .................. 523/105; 128/90; 428/253, 254, 255, 273, 542.8, 913

[56] References Cited

U.S. PATENT DOCUMENTS

| 4,667,661 | 5/1987 | Scholz et al. | 128/90 |
| 4,934,356 | 6/1990 | Klintworth | 128/90 |

*Primary Examiner*—James C. Cannon
*Attorney, Agent, or Firm*—Head & Johnson

[57] ABSTRACT

An orthopedic casting material which is coated on a flexible material as a water-curable prepolymer resin wherein the resin is formed by the reaction of an isocyanate and a polyol where the polyol has a colorant premixed therein and an effective detackifying quantity of one or more hydrophilic bisurethanes is added thereto.

24 Claims, No Drawings

WATER-ACTIVATED ORTHOPEDIC CAST COMPOSITION HAVING COLORANT

RELATED APPLICATIONS

This is a continuation-in-part of U.S. application, Ser. No. 07/452,217 for ORTHOPEDIC CASTING MATERIAL HAVING REDUCED TACK AND REDUCED SLIP, filed on Dec. 18, 1989.

The application herein is related to U.S. application, Ser. No. 07/004,087 for a WATER-ACTIVATED ORTHOPEDIC CAST COMPOSITION HAVING COLORANT, filed on Jan. 15, 1987, now U.S. Pat. No. 4,934,356.

Both of these applications have a common assignee: Carapace, Incorporated.

FIELD OF THE INVENTION

The invention disclosed herein relates to orthopedic bandages comprising a cast forming composition that is used in the preparation of surgical casts designed to immobilize and support portions of the body, e.g. a leg, arm, wrist, neck, and the like. The improvement herein relates to a composition formed as a part of a flexible fabric which when set will be of a color other than natural white, which is combined with an effective amount of one or more hydrophilic bisurethanes to reduce tack and slip ("detackifier") in the casting composition.

BACKGROUND

For many years orthopedic surgeons and other specialists have long worked with Plaster of Paris, almost exclusively, in the preparation of surgical casts. The problems associated with Plaster of Paris as to weight, water damage, x-ray opaqueness, etc. are well documented. Recently, Plaster of Paris has to a large extent been replaced with the development of orthopedic bandages which utilize cast forming compositions and mixtures using water soluble vinyl monomers such as those selected from the group consisting of diacetone acrylamide (DAA), N-isopropylacrylamide (N-IPA) and mixtures thereof wherein the monomers are polymerizable in the presence of water by means of an amine catalyst or a redox catalyst system that comprises an oxidation component and a reducing agent. Such an orthopedic bandage is described in U.S. Pat. No. 3,630,194. The bandages are hardened in a manner similar to the Plaster of Paris bandages by dipping the bandage into tap water which is then formed about the portion of the body to be immobilized or supported. Other prior art orthopedic bandages are found in U.S. Pat. Nos. 4,411,262; 4,376,438; 4,344,423; 4,502,479; and 4,433,680. The resulting hardened bandage has always been of a natural (white) color which is subject to discoloration becoming unsightly and without any fashionable character. The addition of a colorant to the cast material must take into due consideration the effect of the colorant to the cast forming material, its reactiveness, its strength, its shelf life, and possible reaction to the patient. Also, the formation of a homogeneous solution of the polymer must consider the chemical effects involved so as not to radically change the composition or the reactions involved.

The prepolymer treated bandage is soaked in water prior to application to the body member, and the wet bandage is then applied to the body member. After the bandage is applied, the cast is smoothed with a gloved hand and held at certain points until it hardens. Since the resins in the bandage are quite tacky until they cure, the protective gloves worn by the cast applier tend to stick to the bandages. This is disadvantageous since it can lead to unwinding of the cast as layers of the tape pull apart from each other and the cast cannot be molded.

To alleviate the problem of "tackiness" in curable resin-coated bandages, Scholz et al proposed, in U.S. Pat. No. 4,667,661, treating such bandages with certain lubricants to reduce the kinetic coefficient of friction of such sheets to less than about 1.2. The lubricant can be comprised of (a) hydrophilic groups which are covalently bonded to the curable resin, (b) an additive which is incompatible with the curable resin, or (c) a combination of (a) and (b). As noted in the Scholz et al patent (e.g. column 11, lines 21 et seq.), the bandages treated with such lubricants become very slippery, and molding of the cast becomes easy due to the non-tacky nature of the resin. It is also noted in the Scholz et al patent (column 8, lines 45-65) that materials such as mineral oil were evaluated as lubricants and, although they did give a non-tacky and even slippery feeling to the surface of the casting tape which allowed easy application and moldability of the tape to the patient, the effect was transient. On average, Scholz et al report, such materials lasted only a day to a week, apparently due to the dissolution of the oil into the resin.

There exists a need for a bandage material with improved handling properties, i.e. one which is neither too tacky nor too slippery.

SUMMARY

This invention thus combines the use of a colorant in a prepolymer casting material, as well as the use of a detackifying agent therein effectively combining the teachings of said copending applications identified above.

DETAILED DESCRIPTION

It has been found that bandage materials can be prepared by blending with a polyisocyanate prepolymer utilized to coat the bandage material, a hydrophilic bisurethane. More particularly, this invention relates to a prepolymer mixture for use in colored orthopedic casting materials comprising a polyisocyanate prepolymer and an effective detackifying quantity of one or more hydrophilic bisurethanes. This invention also relates to an orthopedic casting material comprising a fabric impregnated and/or coated with said prepolymer mixture.

More particularly, hydrophilic bisurethanes useful as the detackifying additive in this invention are compounds selected from the formulas I and II:

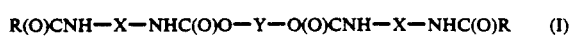

$$R(O)CNH-X-NHC(O)O-Y-O(O)CNH-X-NHC(O)R \quad (I)$$

$$Z-NHC(O)O-Y-O(O)CNH-Z \quad (II)$$

where Y is a hydrophilic polymeric chain having a molecular weight in the range of about 1000 to 8000. O—Y—O can be derived from diols of the general formula (III):

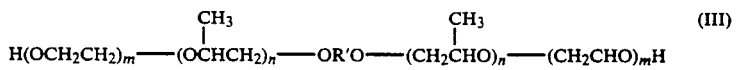

$$H(OCH_2CH_2)_m\text{---}(OCHCH_2)_n\text{---}OR'O\text{---}(CH_2CHO)_n\text{---}(CH_2CHO)_mH \quad (III)$$

where M is an integer of 1 or more and N is 0 or an integer of 1 or more, and R' is —CHCH₂—or —CH(CH₃)CH₂—. If n is 0, the compound of formula III is a poly(oxyethylene) diol. The polymer may be a block copolymer or a random copolymer.

Each X in Formula I and each Z in Formula II may be the same or different and is selected from an aromatic, cycloaliphatic or aliphatic group. In the case of Formula I, the bisurethanes are derived from the above-described polyetherdiols (III) and diisocyanates which can be either aromatic (e.g. toluene diisocyanate, methylene-4,4'-bis(phenylisocyanate)) or cycloaliphatic (e.g. methylene-4,4'-bis(cyclohexyl)diisocyanate, isophorone diisocyanate, 1,4-cyclohexane diisocyanate) or aliphatic (e.g. hexamethylene diisocyanate), or mixtures thereof. In the case of Formula II, the bisurethanes are derived from the above-described polyetherdiols (III) and monoisocyanates which can be aromatic (e.g. phenyl isocyanate), cycloaliphatic (cyclohexyl isocyanate) or aliphatic (butyl isocyanate) or mixtures thereof.

In Formula I, R is derived from monofunctional alcohols such as but not limited to methanol, ethanol, isopropanol, butanol, and lauryl alcohol, or from oxyalkylene adducts of monofunctional alcohols of the general Formula IV:

$$H''\text{---}O\text{---}(CH_2CHO)_q(CH_2CH_2)_mH \quad (IV)$$

where q and m are independently 0 or integers of 1 or more, provided that if one of q and m are 0, the other of q and m is an integer of 1 or more. Best results have been attained with bisurethanes of Formula I where R is derived from methanol or ethanol.

To prepare the bisurethanes of Formula I, one mole of polyether diol is reacted with two moles of diisocyanate to form an isocyanate-terminated prepolymer which is then reacted with two moles of monofunctional alcohol. To prepare the bisurethanes of Formula II, one mole of a polyether diol of the general Formula III is reacted with two moles of monofunctional isocyanate. The synthesis of the bisurethanes can be carried out in solvent or in bulk. Different types of non-reactive solvents can be used, such as cellosolve acetate and dichloromethane. The reaction temperature is critical in the bisurethane preparation and should not exceed 80 degrees C because of possible side reactions. The synthesis should be carried out under inert, dry conditions with dried reagents. Small amounts of benzoyl chloride (0.5-1%) can be used in the preparation of the bisurethanes to control the reaction rate.

The preferred bisurethanes for use in this invention are those of Formulas I and II wherein O—Y—O is derived from a compound selected from the group consisting of polyethyleneoxides, polypropyleneoxides, and random or block ethylene/propylene oxide copolymers. The most preferred hydrophilic group is a polyethylene glycol having a molecular weight in the range of about 3000 to 5000, most preferably about 4000.

The polyisocyanate prepolymer used in this invention comprises a prepolymer derived from polyisocyanate, preferably aromatic, and a reactive hydrogen compound or oligomer. The preferred prepolymer composition comprises modified diphenylmethane diisocyanate, polypropylene glycol, benzoyl chloride stabilizer and dimorpholinodiethylether catalyst. The preferred isocyanate to diol ratio is about 4 to 1 (NCO/OH=4/1). To prolong the shelf life of the material, certain stabilizers such as benzoyl chloride (0.1 to 1.0 wt. %) may be included in the prepolymer, and foam suppressors such as silicone liquids may also be included.

The advantageous non-tacky yet non-slippery properties of the casting materials of this invention are achieved by blending with the polyisocyanate prepolymer an effective detackifying quantity of a hydrophilic bisurethane as described above. Generally, the hydrophilic bisurethane should be blended with the polyisocyanate prepolymer in the amount of about 0.1 to 10%, preferably 0.5 to 5% and most preferably about 2% per weight of the polyisocyanate prepolymer.

The detackifier may be added to the prepolymer prior to reaction with water, during reaction with water, or after the reaction while the cast is still wet. In other instances, the bisurethanes can be added in liquid form to the prepolymer:

1) Combined with the desired colored pigment which has been dispersed in a small amount of the polyol which has been used to make the prepolymer.

2) Combined with the desired colored pigment which has been dispersed in a small amount of the prepolymer.

3) Added directly to the prepolymer which has already been pigmented.

A drum roller or a paddle mixer, under nitrogen, can be used to obtain even distribution of the pigment-/detackifier materials throughout the prepolymer.

Best results according to this invention have been achieved using a polyisocyanate prepolymer which is the reaction product of 56% diphenylmethane diisocyanate (this and all percentages unless otherwise stated being % by weight of the total reaction products), 37.7% polypropylene glycol (Pluracol P710, BASF Chemicals, 0.1% benzoyl chloride, 2.0% dimorpolinyldiethylether catalyst, 0.2% silicone defoaming agent and 4% of a detackifying mixture prepared by contacting 11% 4,4'-diphenylmethane diisocyanate, 0.5% benzoyl chloride and 8.7% poly(oxyethylene) glycol (MW=4000) which reaction is stopped by short by addition of 1.5% ethanol.

The types of fabric upon which a curable polyisocyanate prepolymer is coated or in which such prepolymer may be impregnated have been well described in the art (e.g. U.S. Pat. Nos. 4,667,661 and 4,411,262, the disclosures of which are herein incorporated by reference). The sheet is semi-rigid or flexible and should be porous so that the curing agent, water, may penetrate into the roll of fabric and contact all parts of the resin. Examples of suitable sheets are woven, non-woven or knit fabrics comprised of natural or synthetic fibers. Preferred sheets are knit fiberglass fabrics, although fabrics of cotton and polyester, for example, may also be used.

The openings are in the preferred range of 250-280 mesh-size openings per square inch and preferably 265 openings per square inch. A typical knit fiberglass is that manufactured by MacMurray Fabrics, Inc. The structural strength and textural characteristics as to porosity and thickness are chosen to provide rapid and thorough mixing of the curing agent with the impregnated resin component. A fabric selected is to be thin with a high surface-to-volume ratio. The fabric used is formed in rolls of various widths generally from one to six inches wide and is impregnated with the curable resin material by an environmentally controlled process to eliminate moisture which would otherwise cause the premature hardening and/or low shelf life of the resulting impregnated fabric. The amount of the resin component is controlled such that there is sufficient formation of a strong inter-layer laminate bond but yet will not occlude the porosity and unnecessarily thicken the film and the fabric. The resulting resin coated fabric is formed in a roll wound up on a plastic core and then packaged within an hermetically sealed container. When it is ready for use, the package is opened and the roll is fully immersed in water for sufficient time for the water to seep into the porous material and displace the air. The roll is then unwound during the formation and wrapping of the cast in a manner well known to the orthopedic surgeon or specialist.

The amount of prepolymer/detackifier mixture applied to the fabric must be sufficient for the formation of a stron inter-layer laminate bond but not so much as to occlude the porosity and unnecessarily thicken the resin film which should be thin for rapid and complete hardening. Excessive prepolymer may cause the fabric to be messy to handle because of stickiness or dripping and transfer of resin. The desired resin-to-carrier fabric weight ratio is a function of both the prepolymer viscosity and the surface characteristics of the fabric and is therefore not susceptible to precise quantification; however, an appropriate radio could be easily determined by one skilled in the art.

The materials of this invention are further illustrated by the following examples, which are intended to be illustrative and not limiting of the scope of this invention.

EXAMPLE 1

Preparation of NCO-Terminated Urethane Prepolymers

Using the following general procedure, the NCO-terminated urethane prepolymers set forth in Table I were prepared.

The polyols utilized were dried at 80° C. under vacuum of 103 mm Hg for 24 hours prior to use.

An NCO-terminated urethane prepolymer was prepared by mixing two (2) equivalents of 4,4'-diphenylmethane diisocyanate ("MDI", Mondur M from Mobay Chemical Co.) with one (1) equivalent of polyol. The MDI flakes were weighed into a 500 ml reaction kettle equipped with a dropping funnel, a nitrogen inlet and outlet valve, a mechanical stirrer, heating jacket, and thermometer. The MDI was heated to melting at 70° C. under a dry nitrogen blanket. To the melted MDI was added 0.5 percent by weight of the total formulation (MDI+polyol) of benzoyl chloride. The benzoyl chloride was allowed to mix with the MDI at 70° C. until the mixture became homogeneous. The calculated amount of polyol was added to the stirred MDI-benzoyl chloride mixture at 70° C. in a steady stream. The temperature of the reaction was raised above 80° C., depending on the quantity and rate at which the polyol was added. The reaction was controlled using a water bath. Following the addition of the polyol, the temperature should be maintained at 70° C. The reaction was completed in 3-4 hours.

The progress of the reaction was followed by means of the n-dibutyl amine titration (ASTM D-1638-84). The reaction was considered complete when the determined value of the percent isocyanate in the prepolymer agreed with the theoretical value, calculated based upon the weights of the materials used, within 1%.

TABLE I

Composition and Consistency of Bisurethanes

| Ex. | Polyol, mol | Monofunctional Alcohol, mol | Isocyanate, mol | Consistency |
|---|---|---|---|---|
| 1 | PEG-1000, 1 | EtOH, 2 | MDI, 2 | Solid |
| 2 | PEG-1500, 1 | EtoH, 2 | MDI, 2 | Solid |
| 3 | PEG-4000, 1 | EtoH, 2 | MDI, 2 | Solid |
| 4 | PEG-8000, 1 | EtoH, 2 | MDI, 2 | Solid |
| 5 | PEG-4000, 1 | MeOH, 2 | MDI, 2 | Solid |
| 6 | PEG-4000, 1 | EtOH, 2 | IPDI, 2 | Insoluble Gel |
| 7 | PEG-4000, 1 | — | PI, 2 | Solid |
| 8 | PEG-4000, 1 | — | PI, 2 | Solid |
| 9 | — | Polyoxyethylene derivative of nonyl Phenol, MW 632 | MDI, 1 | Liquid |

PEG-1000 = Poly-G-1000, Olin Chemical
PEG-1500 = Poly-G-1500, Olin Chemical
PEG-4000 = Pluracol E-4000, BASF Chemicals
PEG-8000 = Pluracol E-8000, BASF Chemicals
Polyoxyethylene derivative of nonyl phenol = Surfonic N-95, Texaco Chemicals
MDI = 4,4'-diphenylmethane diisocyanate, Mondur M, Mobay Chemicals
IPDI = isophorone diisocyanate, "IPDI" from Huels America
PI = phenyl isocyanate, "PI" from Aldrich Chemicals Preparation of Bis-Urethane An equivalent amount of 100% ethanol was added to the stirred urethane prepolymer at 70° C. under nitrogen in an excess of 2-3. The kettle was equipped with a water-cooled condenser to prevent evaporation of the alcohol. The alcohol, at room temperature, was added in one portion to the stirred prepolymer by means of a dropping funnel. The reaction between the NCO-prepolymer and the alcohol occurred very quickly at 70° C., and the reaction was completed in two hours. The reaction was again followed by the n-dibutyl amine titration and was considered complete when the present isocyanate in the material was zero. The bis-urethane material was then transferred and stored in a closed glass bottle or metal can.

The bisurethanes prepared as described above were blended with polyisocyanate prepolymer (reaction product of diphenylmethane diisocyanate and polypropylene glycol) at room temperature. Bisurethanes which were solid at room temperature were melted at 70°-80° C. prior to mixing. After standing for twenty-four hours at room temperature, the resulting mixtures were tested for compatibility, viscosity, isocyanate concentration, and tackiness and slip properties.

Tackiness and slip properties were measured according to the following procedure: A tape is coated with the olyisocyanate prepolymer/bisurethane mixture. The coated tape is dipped in water five times. Slip properties are measured by noting the relative slipperiness of rubber gloves to the coated surface.

The test method for determining tackiness is a qualitative test. The resin mixture is applied to four inches of a 1"×5" long tape, leaving one inch of the tape dry. The coated tape is dipped in water, laid flat, and a 1"×4" piece of a rubber glove is firmly pressed to it. One inch of the uncoated portion of the tape is clamped to the ring portion of a ring stand using a clothespin. Afterwards, a five-gram weight on a string is attached to the tape using a paper clip to the rubber glove portion ⅛ inch from the edge. The released weight is allowed to pull the rubber from the tape. The time necessary to completely pull the four-inch strip of rubber from the tape is measured using a stopwatch.

The properties of the resulting casting resins are set forth in Table II.

TABLE II

| Example | Concentration Bisurethane, % | Viscosity cps | Peel time sec. | % NCO |
|---|---|---|---|---|
| Control | 0 | 13,400 | 15 | 11.27 |
| 1 | 2 | 12,800 | 8 | 9.60 |
| 2 | 2 | 11,400 | 5 | 10.31 |
| 3 | 2 | 17,400 | 6 | 10.33 |
| 4 | 2 | 102,600 | v. long | 9.92 |
| 5 | — | 23,400 | 12 | 10.02 |
| 6 | — | — | — | — |
| 7 | 2 | 13,400 | 3.5 | 10.78 |
| 8 | 2 | 20,600 | 2.2 | 8.59 |
| 9 | 2 | 22,200 | 7.0 | 8.75 |

An additional object of this invention is to provide a novel orthopedic bandage wherein the resultant hardened cast is of a color other than natural (white) which occurs as a result of the prior art methods and composition.

This portion of the invention also has for its object to provide a novel method of forming a polymer orthopedic cast composition which is to be coated upon a flexible fabric and in particular to a method of mixing a colorant with the composition. In particular, the composition being a water-curable prepolymer resin that is formed by the reaction of an isocyanate and a polyol wherein the polyol is premixed with a colorant such as pink or blue. In use the components of the composition are such that an orthopedic surgeon or specialist need only dip the bandage in water in order to initiate polymerization and prepare the bandage for use. The detackifying agents, described above, can be added before, during, or after wetting the bandage.

Another object of the invention is to provide a method of pre-preparation of a polypropylene oxide colored polyol for use as a part of a water-cured polyisocyanate prepolymer orthopedic cast resin. The steps of the method comprise first separating a minor portion of the polyol from the total batch of the polyol. A colorant is slowly added and mixed with the minor portion of the polyol. The minor portion may be heated and mixing continued until the colorant has dissolved in the minor portion. Thereafter, the minor portion of colored polyol is added and mixed with the remaining major batch of said polyol which is thereafter added to and mixed with said isocyanate.

The resulting invention provides an orthopedic cast of attractive fashionable color that does not interfere with the shelf life of the unpolymerized composition or interfere with the high strength characteristics of the cast composition, or create side effects upon the patient.

According to the preferred embodiment of the present invention, the resin composition is comprised of two parts, premix "A" that is reacted with premix "B". Premix "A" is comprised of an isocyanate resin such as that sold by the Upjohn Company under the registered trademark "Isonate 143L," a form suppressing material such as Union Carbide SAG-47, a silicone anti-foam compound, or Dow Corning DB-1000 silicone fluid and a preservative or stabilizer such as benzoyl chloride to prolong shelf life. As noted above, the detackifier may be added at this point, or later during the addition of water or after the addition of water.

Premix "B" is comprised of a polypropylene oxide polyol such as is available under the registered trademark "Pluracol P-710" from BASF Wyandotte, a catalyst such as Dimethylethanolamine (DMEA) and/or an amino/glycol mixture such as a material identified under the registered trademark "Niax A-1" which is used to control the reactivity of the resin once it is exposed to water.

In the preparation of premix "A", the Isonate 143 L is measured and put into a reaction vessel under vacuum. When the material has been totally added, the vacuum is released, and dry nitrogen is then purged into the reaction vessel. While the reaction vessel is still being purged with dry nitrogen, the defoaming material is added and mixed into the Isonate 143 L. Mixing continues for at least 10 minutes with the benzoyl chloride being slowly added to the vessel which is still being purged with the dry nitrogen and allowed to mix for at least 20 minutes. The purpose of the dry nitrogen is to prevent intrusion of moisture into the premix.

In preparing premix "B", a minor portion, e.g. 10%, is separately removed while the remaining portion is added to a second reaction vessel. The aforesaid minor portion is then taken to a separate mixing vessel where the proper weight of a colorant is slowly added and mixed with the minor portion of polyol. This mixture can be heated during mixing until, in any event, the colorant material has completely dissolved within the minor portion. Thereafter, this solution is added to the second reaction vessel where a vacuum of 20 to 30 inches of mercury is applied and mixing begun for at least four hours. Once the Pluracol P-710 has been vacuum dried, the vacuum is released, and the nitrogen is purged into the second reaction vessel. The addition of catalyst(s) in a measured amount is then added to the premix under the nitrogen purge, and mixing continues for thirty minutes to insure a homogenous solution.

With the premix "B" reaction vessel under a dry nitrogen purge, its contents are slowly added and mixed with premix "A" in its reaction vessel which is also under a dry nitrogen purge. The increments of addition are such that it takes 20-25 minutes total time. Once the addition is complete, the final mixing action should be continued for one to one and one-half hours under a dry nitrogen purse.

The resin used in the casting material may be any curable resin such as those described in the aforesaid prior art patents which will satisfy the functional requirements of an orthopedic cast such that the addition of a colorant material or non-functional additive to the resin will still maintain the characteristics of a desirable orthopedic cast that is not harmful to either the patient or the person applying the cast. In addition, the resin and the added colorant as specified in this invention must be sufficiently compatible to ensure rapid hardening of the cast yet permit sufficient working time to apply and shape the cast.

The preferred resins are those cured with water. A number of classes of water-curable resins known in the art are suitable, including polyurethanes, cyanoacrylate esters and, when combined with moisture sensitive catalyst, epoxy resins and prepolymers terminated at their ends with trialkoxy- or trihalo-silane groups. Other useful resins are polyethers, polyesters, MDI, and TDI polymerics. Although there are other resin systems useful to the purposes of this invention that are cured by other than the use of water, the preferred resin is one that is water curable.

Although the preferred colorants are pink and blue, it is to be understood that other colors are inclusive of use in this invention. Preferably, a blue colorant is formed of a combination of Orasol Blue GN in combination with Orasol Pink 5 BLG which are manufactured and sold under those trademarks by Ciba-Geigy. The concentrations are within the ranges of 0.001% to 5.0%, preferably 0.07% by weight of the blue, and within the ranges of 0.001% to 5.0%, preferably 0.007% by weight of pink. A pink coloring is formed by Orasol Pink 5 BLG, a monoazo chrome complex, manufactured and sold under that trademark by Ciba-Geigy. The concentration used in the invention is 0.01% by weight.

What is claimed is:

1. A colored orthopedic cast-forming composition for immobilizing a patient's body or portions thereof, said composition comprising:
   a water-curable prepolymer resin formed by the reaction of one reactant with another reactant wherein said latter reactant was one to which a colorant had been intermixed prior to conducting said reaction, said colorant being one which is patient non-reactive and does not interfere with the shelf life and strength or rapid-hardening characteristics of the cast forming composition; and
   an effective detackifying quantity of one or more hydrophilic bisurethanes.

2. The composition of claim 1 wherein said colorant is blue.

3. The composition of claim 2 wherein said blue colorant is formed of 0.07% by weight of blue colorant and 0.007% by weight of pink colorant.

4. The composition of claim 1 wherein said colorant is pink.

5. The composition of claim 4 wherein said pink colorant is in concentration of 0.01% by weight.

6. The composition of claim 1 in which said prepolymer resin comprises the reaction product of diphenylmethane diisocyanate and polypropylene glycol.

7. The composition of claim 1 wherein said hydrophilic bisurethanes are selected from compounds of the formulas I and II:

R(O)CNH—X—NHC(O)O—Y—O(O)CNH—X—NHC(O)R    (I)

Z—NHC(O)O—Y—O(O)CNH—Z    (II)

where Y is a hydrophilic polymeric chain having a molecular weight in the range of about 1000 to 8000; each X in formula I and each Z in formula II may be the same or different and is selected from aromatic, cycloaliphatic or aliphatic groups; and R is derived from monofunctional C1-C6 alcohols of the general formula IV:

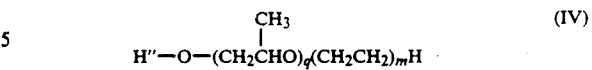

where q and m are independently 0 or a positive integer provided that if one of q or is 0, the other of q or m is a positive integer.

8. The composition of claim 7 where O—Y—O is derived from diols of the general formula (III):

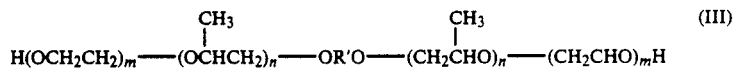

where m and n are independtly 0 or a positive integer, and R' is —CHCH$_2$—or CH(CH$_3$)CH$_2$—.

9. The composition of claim 8 wherein the diol is a polyethylene glycol having a molecular weight in the range of about 3000 to 5000.

10. The composition of claim 9 wherein the polyethylene glycol has a molecular weight of about 4000.

11. The composition of claim 7 wherein the bisurethane has the formula I.

12. The composition of claim 7 wherein the bisurethane has the formula II.

13. The composition of claim 7 wherein (O)CN-H—X—NHC(O) is derived from a diisocyanate selected from the group consisting of toluene diisocyanate, methylene-4,4'-bis(phenylisocyanate),methylene-4,4'-bis(cyclohexyl)diisocyanate, isophorone diisocyanate, 1,4-cyclohexane diisocyanate, hexamethylene diisocyanate, and mixtures thereof.

14. The composition of claim 11 wherein Z-NHC(O) and (O)CNH-Z are derived from a monoisocyanate selected from the group consisting of phenyl isocyanate, cyclohexyl isocyanate, butyl isocyanate and mixtures thereof.

15. The composition of claim 12 wherein said Z-NHC(O) and (O)CNH-Z are derived from a monoisocyanate selected from the group consisting of phenyl isocyanate, cyclohexyl isocyanate, butyl isocyanate and mixtures thereof.

16. The composition of claim 11 wherein R" is derived from methanol or ethanol.

17. The composition of claim 11 where O—Y—O is derived from a polyethylene glycol having a molecular weight in the range of about 3000 to 5000, X is derived from methylene-4,4'-bis(phenylisocyanate), and R" is derived from ethanol.

18. The composition of claim 17 where O—Y—O where is derived from a polyethylene glycol having a molecular weight of about 4000.

19. The composition of claim 12 where O—Y—O is derived from a polyethylene glycol having a molecular weight in the range of about 3000 to 5000, X is derived from methylene-4,4'-bis(phenylisocyanate), and R is derived from ethanol.

20. The composition of claim 19 wherein O-Y-O is derived from n-polyethylene glycol having a molecular weight of about 4000.

21. The composition of claim 1 where said hydrophilic bisurethane is blended with said prepolymer in a quantity of about 0.5 to 5 weight % based on the weight of said prepolymer.

22. The composition of claim 1 wherein said composition is coated on a flexible fabric.

23. The composition of claim 22 wherein said fabric is a knit fiberglass of mesh size within the range of 250–280 openings per square inch.

24. The composition of claim 22 wherein said fabric is fiberglass of mesh size having 265 openings per square inch.

* * * * *